United States Patent
Vinogradov

(10) Patent No.: US 7,821,258 B2
(45) Date of Patent: *Oct. 26, 2010

(54) METHOD AND SYSTEM FOR GENERATING AND RECEIVING TORSIONAL GUIDED WAVES IN A STRUCTURE

(75) Inventor: Sergey A. Vinogradov, San Antonio, TX (US)

(73) Assignee: IHI Southwest Technologies, Inc., San Antonio, TX (US)

(*) Notice: Subject to any disclaimer, the term of this patent is extended or adjusted under 35 U.S.C. 154(b) by 398 days.

This patent is subject to a terminal disclaimer.

(21) Appl. No.: 11/970,378

(22) Filed: Jan. 7, 2008

(65) Prior Publication Data

US 2009/0174399 A1 Jul. 9, 2009

(51) Int. Cl.
*G01N 27/82* (2006.01)
(52) U.S. Cl. ...................................... 324/240
(58) Field of Classification Search ............... 324/209, 324/217, 219, 220, 221, 228, 234, 235, 236, 324/237, 238, 239, 240, 262
See application file for complete search history.

(56) References Cited

U.S. PATENT DOCUMENTS

| | | | |
|---|---|---|---|
| 4,497,209 A | 2/1985 | Kwun et al. | |
| 4,711,120 A | 12/1987 | Kwun et al. | |
| 4,979,125 A | 12/1990 | Kwun et al. | |
| 5,180,969 A | 1/1993 | Kwun et al. | |
| 5,456,113 A | 10/1995 | Kwun et al. | |
| 5,457,994 A | 10/1995 | Kwun et al. | |
| 5,581,037 A | 12/1996 | Kwun et al. | |
| 5,747,696 A | 5/1998 | Kwun et al. | |
| 5,767,766 A | 6/1998 | Kwun | |
| 5,821,430 A | 10/1998 | Kwun et al. | |
| 5,970,434 A | 10/1999 | Kwun et al. | |
| 6,000,288 A | 12/1999 | Kwun et al. | |
| 6,134,947 A | 10/2000 | Kwun | |
| 6,201,391 B1 | 3/2001 | Kwun et al. | |
| 6,205,859 B1 | 3/2001 | Kwun et al. | |
| 6,212,944 B1 | 4/2001 | Kwun et al. | |
| 6,294,912 B1 | 9/2001 | Kwun | |
| 6,295,677 B1 | 10/2001 | Kwun et al. | |

(Continued)

OTHER PUBLICATIONS

Cho et al., High Frequency Torsional Modal Testing of a Long Cylinder by Magnetostriction, Appl. Phys. Let. 91 (2007), pp. 071908-1-3.*

(Continued)

*Primary Examiner*—Kenneth J Whittington
(74) *Attorney, Agent, or Firm*—Gunn, Lee & Cave, P.C.

(57) ABSTRACT

A method is shown for magnetostrictive testing of structures using magnetostrictive techniques. A torsional guided wave is generated in the structure either directly, or through a magnetostrictive strip dry coupled or bonded to the structure. A permanent magnetic field is created by either permanent magnets or DC current for a permanent bias in a bias direction in the magnetostrictive strip and/or structure. By pulsing the magnetic field with an AC current pulse, a torsional guided wave will flow through the structure in the same direction as the permanent bias. By saturating the permanent magnetic field, a maximum torsional guided wave is reflected from defects in the structure to given an improved signal to noise ratio.

19 Claims, 5 Drawing Sheets

U.S. PATENT DOCUMENTS

| | | | |
|---|---|---|---|
| 6,373,245 | B1 | 4/2002 | Kwun et al. |
| 6,396,262 | B2 | 5/2002 | Kwun et al. |
| 6,404,189 | B2 | 6/2002 | Kwun et al. |
| 6,424,150 | B2 | 7/2002 | Kwun et al. |
| 6,429,650 | B1 | 8/2002 | Kwun et al. |
| 6,624,628 | B1 | 9/2003 | Kwun et al. |
| 6,779,409 | B1 | 8/2004 | Kwun et al. |
| 6,815,948 | B1 | 11/2004 | Kwun et al. |
| 6,917,196 | B2 | 7/2005 | Kwun et al. |
| 6,925,881 | B1 | 8/2005 | Kwun et al. |
| 6,968,727 | B2 | 11/2005 | Kwun et al. |
| 7,019,520 | B2 | 3/2006 | Kwun et al. |
| 7,131,339 | B2 | 11/2006 | Kwun et al. |
| 7,573,261 | B1 * | 8/2009 | Vinogradov ................ 324/240 |
| 2007/0090904 | A1 * | 4/2007 | Kim et al. ................... 335/205 |

OTHER PUBLICATIONS

Kim et al., Shear Horizontal Wave Transduction in Plates by Magnetostrictive Gratings, Journ. of Mech. Sci. and Tech. 21 (2007), pp. 693-698.*

Piezoelectricity—Wikipedia, the free encyclopedia (9 pages) http://en.wikipedia.org/wiki/Piezoelectricity.

SwRI wins R&D 100 Award for MsS Heat Exchanger Probe (2 pages), Southwest Research Institute (SwRI) 2006 News Release, San Antonio, TX.

Magnetostrictive Materials (1 page), Aviation Research http://virtualskies.arc.nasa.gov/research/youDecide/magnetoStrictive.html.

Russel, J, Smaller, Lower Cost Magnetostrictive Position Sensors Open Up Comsumer and Professional Product Applications (7 pages), Technical Paper, MTS Systems Corp., Cary, NY.

Magnetostrictive Linear Position Work (4 pages), How They Work http://www.sensorland.com/HowPage024.html.

Caulkins, F., et al, Overview of Magnetostrictive Sensor Technology (11 pages), Journal of Intelligent Material Systems and Structures, vol. 18, Oct. 2007.

Diagnosing Engine Problems with Magnetostrictive Sensors (2 pages), SwRI Magnetostrictive Sensors, http://www.swri.org/3pubs/brochure/d17/magneto/diagnosis.htm.

Magnetic Domains—Wikipedia, the free encyclopedia (3 pages) http://en.wikipedia.org/wiki/Magnetic_domain.

Magnetostriction—Wikipedia, the free encyclopedia (2 pages) http://en.wikipedia.org/wiki/Magnetostriction.

Why does the transformer hum?, Magnetostriction htpp://hyperphysics.phy-astr.gsu.edu/hbase/solids/magstrict.html.

Magnetostriction and Magnetostrictive Materials (2 pages) http://aml.seas.ucla.edu/research/areas/magnetostrictive/mag-composites/Magnetostriction....

Undestanding Transformer Noise (6 pages), Federal Pacific.

Welcome to Magnetostrictive Transducers, Actuators, and Sensors @ Iowa State University . . . (4 pages) http://www.publc.iastate.edu/~terfenol/homepage.html.

Kwun, H., Back in Style: Magnetostrictive Sensors* (8 pages), SwRI Magnetostrictive Sensors http://www.swri.org/3pubs/brochure/d17/magneto/magneto.htm.

Cheong, et al, Comparison of an Array of EMATs Technique and a Magnetostrictive Sensor Technique for a Guided Wave Inspection of a Pipe (4 pages),http://www.scientific.net.

* cited by examiner

METHOD AND SYSTEM FOR GENERATING AND RECEIVING TORSIONAL GUIDED WAVES IN A STRUCTURE

1. BACKGROUND OF THE INVENTION

This invention relates to a method and apparatus for generating and receiving torsional guided waves in a structure using Wiedmann and inverse Wiedmann effect more particularly, where the direction of propagation of the torsional guided waves and the bias of the permanent magnet are in the same direction.

2. BRIEF DESCRIPTION OF THE PRIOR ART

As computer technology has advanced, so has the technology related to sensors. Sensors provide the input for the computers to use in signal processing. Just as computers are used in every aspect of our daily life, computers are also used in evaluating structures to determine if the structures are safe, or if the structures have defects that may impair their safety. One of the problems in evaluating structures using sensors and computers is that not all parts of the structure are available for inspection to determine defects. For example, a bridge may have cables or beams that are inaccessible. Another example may be a containment vessel at a nuclear power plant where major portions of is the vessel are buried underground and inaccessible. A further example may be pipes buried underground that are inaccessible.

While many other methods of inspection of inaccessible structures has been developed, one method that is still being developed is the use of magnetostrictive sensor technology to locate defects in inaccessible structures. A good article giving the current state of the art of magnetostrictive sensor technology is "Overview of Magnetostrictive Sensor Technology," *Journal of Intelligent Material Systems and Structure*, Vol. 18, October 2007, by Frederick T. Calkins, Alison B. Flatau and Marclo J. Dampino. In a nutshell, magnetostrictive materials convert magnetic energy to mechanical energy and visa-versa. If a magnetostrictive material is magnetized, it strains in the direction of magnetization. If an external force produces a strain on the magnetostrictive material, the magnetic state of the magnetostrictive material will change.

A good explanation of the physical changes in the magnetostrictive material in response to rapid magnetization or demagnetization is contained in U.S. Pat. No. 6,917,196 to Kwun, et al, more particularly, the explanation in conjunction with FIGS. 13A through 13C contained therein. Examples of good magnetostrictive materials are as follows:

Cobalt
Iron
Nickel
Ferrite
Terfenol-D
Metglass

Magnetostrictive materials were actually discovered in the 1840's by James Prescott Joule when he noticed that iron changed length in responses to changes in magnetism and named the phenomena the Joule effect. What occurs is the magnetic domains within the material align with the magnetic field causing the expansion. Similarly, when a magnetostrictive material is strained (stretched or compressed), its magnetic energy changes. This is the opposite of magnetostrictive action and the phenomena is called the Villari effect.

Some of the advantages of using sensor made of magnetostrictive materials is the sensors can operate at higher temperatures than other types of sensors. Also the magnetostrictive materials can undergo higher strains with lower input voltages than other types of sensors.

Conventional magnetostrictive sensor techniques for generation of torsional guided waves use Wiedmann effect and require both permanent and alternating magnetic fields. The permanent and alternating magnetic fields may be applied directly to the specimen, or to a magnetostrictive strip with enhanced magnetostriction, which magnetostrictive strip is bonded or dry coupled to the specimen. The orientation of the permanent magnetic field determines the orientation of the permanent bias field, which in turn determines the initial orientation of the magnetic domains in the structure and/or strip.

The orientation of the alternating magnetic field is different from the permanent bias field. To elicit movement of the magnetic domain in the conventional manner, an AC which establishes a variable AC magnetic bias. The angle between the variable AC bias and the permanent magnetic field bias is 90°. This provides for magnetic domains to be aligned in such a direction that the torsional guided wave will be propagated in the direction perpendicular to the magnetic field bias. In the traditional way of generating a torsional guided wave, the orientation of the AC coil is coincident with the orientation of the magnetostrictive strip, and perpendicular to the direction of torsional guided wave propagation.

The major disadvantage of the method described hereinabove is with establishing a permanent magnetic bias field in cases where the magnetostrictive strip has significant length. In a majority of the cases, only residual magnetism of the magnetostrictive strip can be used for initial orientation of magnetic domains in the direction of the permanent magnetic field bias. Due to interference from the AC magnetic field and the residual magnetic fields, the strength of the residual fields tend to decrease, which reduces the signal to noise ratio of the whole system.

OBJECTS OF THE INVENTION

It is an object of the present invention to provide a method of generating and receiving torsional guided waves with increased signal to noise ratio.

It is another object of the present invention to use magnetostrictive techniques that have a variable magnetic field and a permanent magnetic field that are switched, but keep the same pattern and direction of domain movement, which sets the initial orientation of the magnetic domains in the direction of the torsional guided wave propagation.

It is another object of the invention to use inexpensive magnetic materials on a magnetostrictive strip when creating a permanent bias field in the strip for torsional guided wave propagation.

It is still another object of the present invention to be able to switch between permanent magnets and a DC circuit along a magnetostrictive strip to establish a permanent magnetic bias field for generating torsional guided waves.

It is a further object of the present invention to use either dry coupling or bonding of a magnetostrictive strip to a structure to create torsional guided waves in the structure with a permanent magnetic field bias in the direction of propagation of the torsional guided waves.

In the present invention, a permanent magnetic field is created in a magnetostrictive strip. The permanent magnetic field has a magnetic bias aligned with a permanent magnet. A pulse generator creates an AC current that is delivered through a transmitter to a coil that is wound perpendicular to the permanent magnetic field, and adjacent to the magnetostrictive strip. By applying an AC current to the coil, torsional waves are propagated in the magnetostrictive strip in the same direction as the bias created by the permanent magnetic field.

The magnetostrictive material may be the entire structure, or it may be magnetostrictive strip either dry coupled or bonded to the structure in which the torsional guided waves are propagated. In either event, if a defect is encountered by the torsional guided wave in the structure, a torsional guided wave is reflected back. The reflected torsional guided wave is detected by the coil by what is called the inverse Wiedmann effect. The Villari effect is sensed by the transmitter/receiver. The reflected torsional guided wave signal is then run through a signal conditioner, signal processor and signal analysis to determine size and location of the defect. Once that is determined, the information can be conveyed to the user by any traditional means, such as a signal recording device.

It is important to realize that if the structure is a ferromagnetic material, a magnetostrictive strip may not be necessary. However, certain magnetostrictive materials have enhanced magnetostrictive characteristics. Many times it is good to use a magnetostrictive strip with enhanced magnetostrictive characteristics even if defects are being measured in ferromagnetic materials.

It is important that the magnetostrictive strip be saturated along its entire length. This can be accomplished by either a large magnet, a series of small magnets, or by flowing a DC current through the AC windings. It has been found to be very cost effective to use a series of small magnets along the magnetostrictive strip.

The magnetostrictive strip can be arranged in any configuration, including in a circle, with the DC current flowing through windings wound around the outside of the magnetostrictive strip. Simultaneously, the alternating current wire would be wound around the magnetostrictive strip perpendicular to the DC windings. This is very effective in propagating torsional guided waves along a pipe. Also, the DC current magnetic field could be replaced by a magnetic belt that wraps around the outside of the magnetostrictive strip. It is important that the belt be magnetized along its short axis versus along its elongated axis.

In another embodiment, a large permanent magnet could be located inside of a circular arranged shielding strip with the AC current winding therearound. This would be located in a pipe made of a magnetostrictive material. The large magnets would saturate the area of the pipe around the shielding strip and the portion of the AC current adjacent the pipe would initiate the torsional Again, this could be used for creating torsional guided waves along a pipe.

By using the mode of torsional guided waves where the permanent magnetic field has a bias in the same direction as propagation of the torsional guided waves, an increased signal to noise ratio is obtained over other conventional methods.

DETAILED DESCRIPTION OF THE PREFERRED EMBODIMENT

Figure 1:
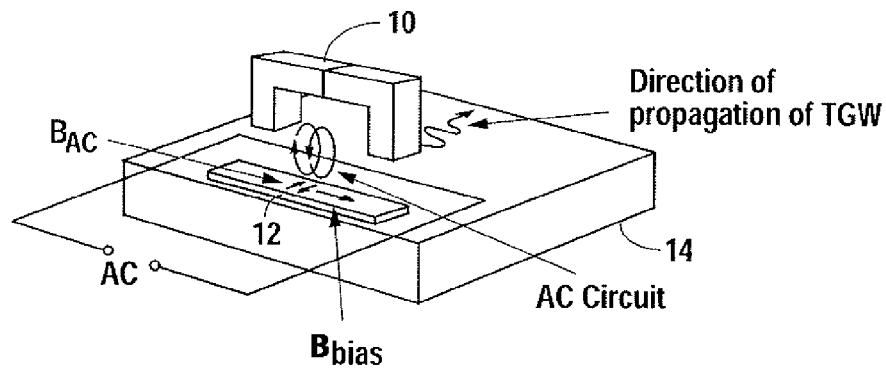
FIG. 1 is a pictorial view of the prior art showing a torsional guided wave with a permanent magnetic field bias and an AC current to generate a magnetic impulse therein.

Referring to FIG. 1, the conventional method of using magnetostrictive techniques to generate torsional guiding waves using both permanent and alternating magnetic fields is shown. A permanent magnet 10 generated a permanent magnetic bias labeled "$B_{bias}$" in the direction indicated by the arrow. When an alternating current (AC) flows adjacent to (or through) the magnetostrictive strip 12, a variable magnetic bias represented by "$B_{AC}$" is generated back and forth in the direction indicated by the arrows. The magnetostrictive strip 12 may be either dry coupled or bonded to the structure 14 under test. If the structure 14 under test has good magnetostrictive characteristics, it may be possible to eliminate the magnetostrictive strip 12.

The angle between the permanent magnetic field $B_{bias}$ and the alternating field $B_{AC}$ is at 90°. Therefore, when an impulse alternating current is applied to the AC circuit shown in FIG. 1, torsional guided waves will be generated and propagated in the direction indicated in structure 14.

The major disadvantage of the prior art shown in FIG. 1 is when establishing a permanent magnetic $B_{bias}$ where the magnetostrictive strip 12 is long. In most cases, only residual magnetism in the magnetostrictive strip 12 can be used for the initial orientation of the magnetic domains within the magnetostrictive strip 12 in the direction of the permanent magnetic $B_{bias}$. Due to interference by the alternating current and residual magnetic fields, the strength of the residual magnetic field tends to decrease, which decreases the signal to noise ratio of the entire system.

Figure 2:
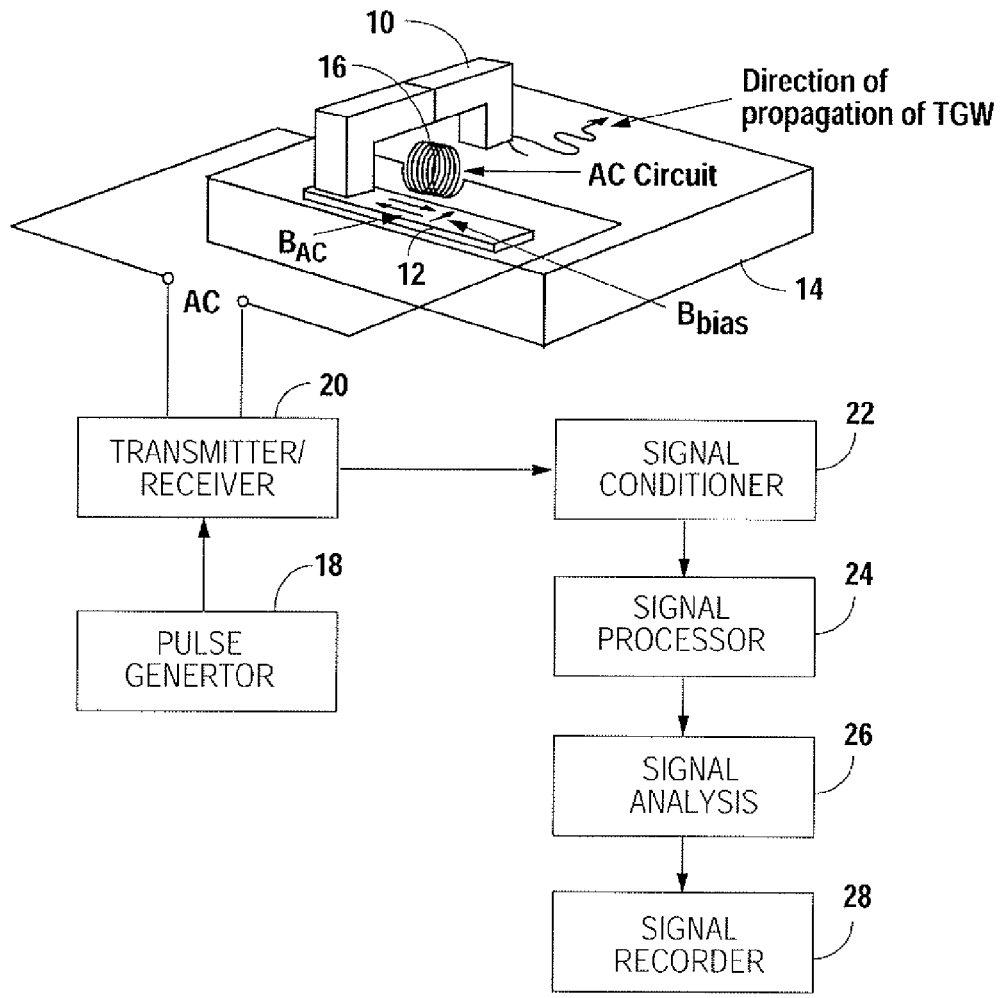
FIG. 2 is a system diagram of the present invention with the torsional guided wave shown in a pictorial view, the direction of propagation of the torsional guided waves being in the same direction as the permanent magnetic field bias.

Referring now to the present invention as shown in FIG. 2, the same numbers will be used to designate similar components where applicable. The magneto strictive strip 12 is again either dry coupled or bonded to the structure 14. If structure 14 has good magnetostrictive properties, it may be possible to eliminate the magnetostrictive strip 12. However, different from FIG. 1, in FIG. 2 the permanent magnet 10 is located perpendicular to the magnetostrictive strip 12. This creates a permanent magnetic field $B_{bias}$ in the direction indicated. Also, the AC circuit is changed so that an AC coil 16 is located immediately adjacent to the magnetostrictive strip 12, but perpendicular to the permanent magnet 10. This generates an alternating bias $B_{AC}$ in the directions indicated which is perpendicular to the magnetic field $B_{bias}$. Hence, when a pulsed alternating current flows through AC coil 16, torsional guided waves propagate in structure 14 in the direction indicated.

In a completed system, after the permanent magnet 10 is located adjacent to, but perpendicular with, the magnetostrictive strip 12, a permanent magnetic field $B_{bias}$ is created. With a pulse generator 18 creating an AC pulse that is fed through transmitter/receiver 20 to the AC coil 16, an impulse of alternating current is created in the AC coil 16. This impulse of alternating current in the AC coil 16 creates the alternating magnetic bias $B_{AC}$ in the magnetostrictive strip 16, which in turn causes the torsional guided waves to propagate in the direction indicated. Of particular importance is that the direction of propagation of the torsional guided waves is the same as the direction of permanent magnetic field $B_{bias}$.

Assuming there is some defect in structure 14, a reflected torsional guided wave will be reflected back towards the magnetostrictive strip 12. The reflected torsional guided wave will be felt in the magnetostrictive strip 12 through what is known as the inverse Wiedemann effect which will cause a mechanical impulse felt in AC coil 16. The reflected torsional guided wave signal detected in AC coil 16 is received by transmitter/receiver 20 and fed to signal conditioner 22. After the signal is properly conditioned, it is fed to a signal processor 24 to process the signal plus a signal analyst 26 to analyze the signal. By use of the combination of the signal conditioner 22, signal processor 24 and signal analysis 26, the defect in the structure 14 can be located and its size approximated. This information can be conveyed to the user by any conventional means including being recorded in the signal recorder 28.

The permanent magnet 10 can be divided into a series of smaller magnets located along the magnetostrictive strip 12 to ensure that the magnetostrictive strip 12 is fully saturated. A set of relatively small bias magnets capable of generating a saturation level of a permanent magnetic $B_{bias}$ in the magnetostrictive strip 12 is fairly inexpensive.

Also, the AC coil 16 could be split into a set of coils connected in either parallel or series arrangement for better performance. It is important that the magnetostrictive strip 12 be fully saturated at the time it is hit with the impulse of alternating current to create magnetic field $B_{AC}$ to ensure the maximum size of torsional guided wave. The maximum size of torsional guided wave also ensures the maximum size of any reflected torsional guided wave due to any defects. It is important that the torsional guided wave and any reflected torsional guided waves be of the maximum size possible to improve the signal to noise ratio.

Figure 7:
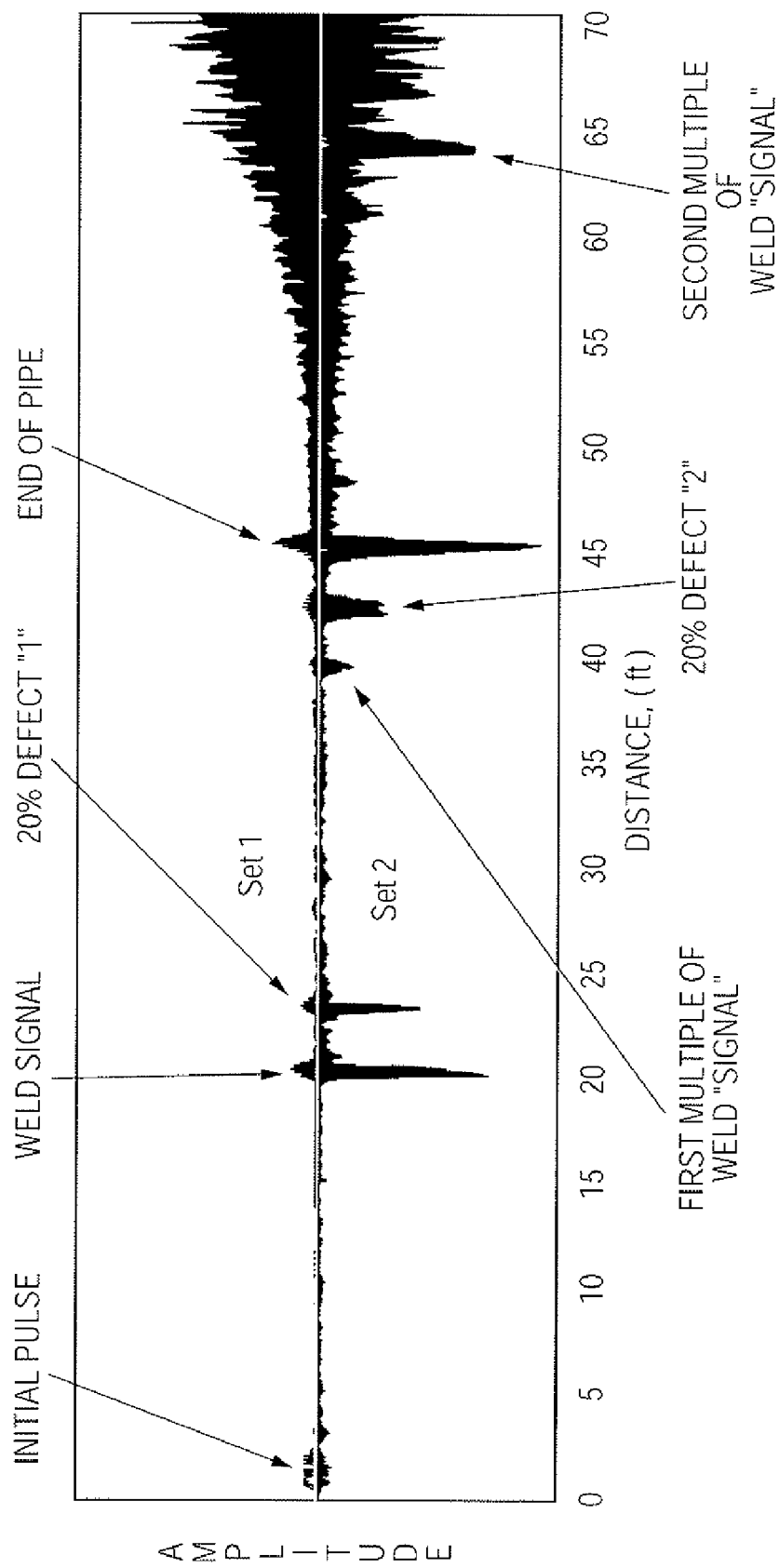
FIG. 7 shows two sets of data on the same pipe with Set 1 using traditional torsional guided waves and Set 2 using the present invention for an increased signal to noise ratio.

By use of the system as shown in FIG. 2 for the direction of propagation of the torsional guided waves is in the same direction as the magnetic field $B_{bias}$, a much greater signal to noise ratio is obtained. In typical examples, FIG. 7 illustrates two sets of data obtained on the same specimen. Using a system similar to the prior art shown in FIG. 1, the Set 1 data of FIG. 7, was obtained. "Set 1" data is the upper half of FIG. 7. An initial pulse was applied by the AC circuit to a magnetostrictive strip 12 having a permanent magnetic $B_{bias}$ therein as shown in FIG. 1. A weld signal was detected in Set 1 data, as well as 20% defect "1" shown in Set 1 data. The end of the pipe is also clearly shown in Set 1 data.

However, when the same pipe was tested using the present invention shown in FIG. 2, the Set 2 data was obtained as illustrated in the bottom half of FIG. 7. Again, the initial pulse was the same. However, the weld signal is over four times larger utilizing the invention shown in FIG. 2 were the permanent magnetic field $B_{bias}$ is the same as the direction of propagation of the torsional guided waves. Also, the 20% defect "1" is about four times larger in Set 2 data as it is in from the prior art shown in Set 1 data of FIG. 7. A first multiple of the weld signal can also be seen in the Set 2 data. Interestingly, the Set 2 data also shows a 20% defect "2" that is almost invisible in the Set 1 data. Clearly, the signal to noise ratio in the Set 2 data as generated by a system similar to FIG. 2 is much greater than the signal to noise ratio of the Set 1 data as generated by the prior art.

Figure 3:
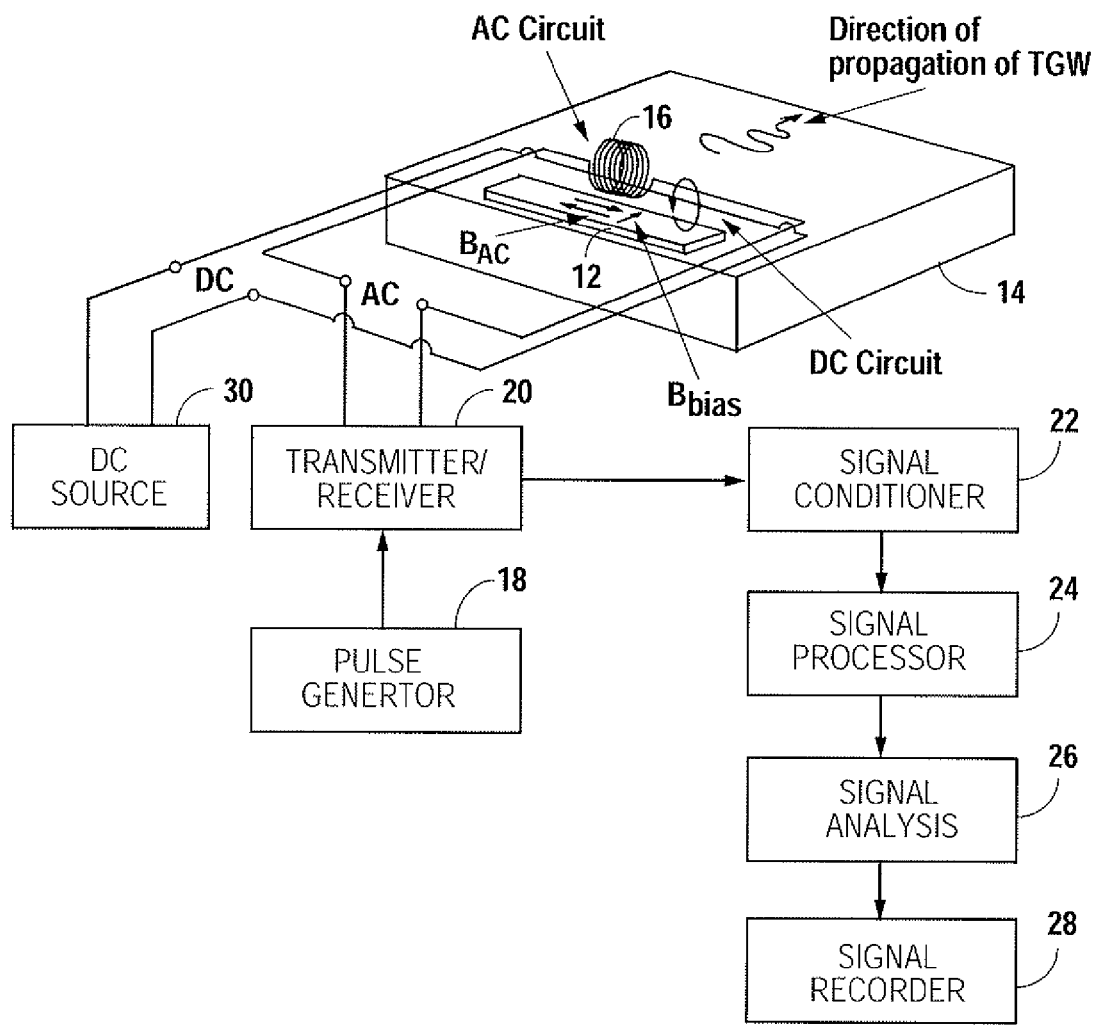
FIG. 3 is the same as FIG. 2 except the permanent magnet of FIG. 2 has been replaced with a source of DC current to create a permanent magnetic field.

FIG. 3 shows an alternative embodiment of FIG. 2 where the permanent magnet 10 is replaced by a DC source 30 to create the permanent magnetic field $B_{bias}$. Otherwise, like numbers are used to designate like elements in FIG. 3 as was shown in FIG. 2. Again, the important thing is that the magnetostrictive strip 12 should be fully saturated from the DC source 30 to ensure the maximum size of the torsional guided wave upon being hit by an impulse magnetic field caused by an impulse alternating current through AC coil 16.

Figure 4:
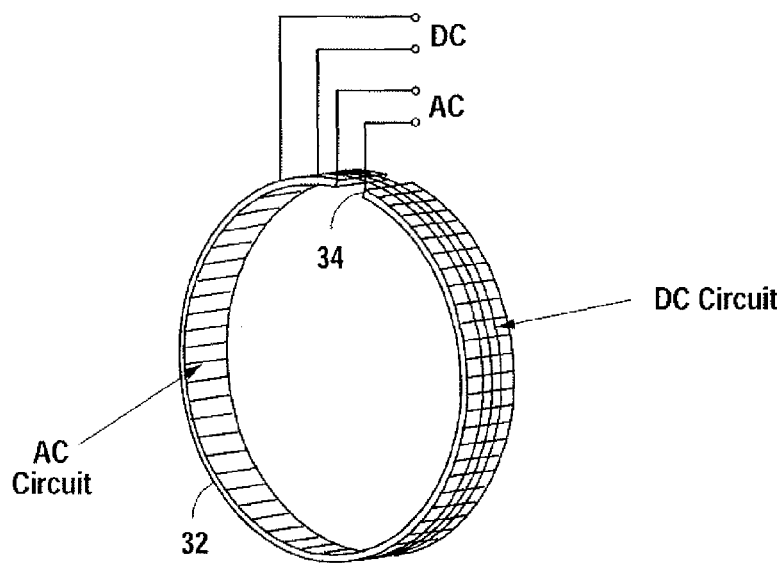
FIG. 4 is an alternative view of the magnetostrictive strip with AC current and DC current windings wrapped therearound, but in perpendicular directions, to create a permanent magnetic field bias and a magnetic impulse therein.

In checking a tubular type structure for defects, a circular magnetostrictive strip 32 may be used with a gap 34 between the two ends thereof as shown in FIG. 4. The control circuit could be identical to the control circuit as shown in FIG. 3. The DC circuit is wound around the outside of the circular magnetostrictive strip 32. However, the AC circuit is wound around the short axis of the magnetostrictive strip 32, perpendicular to the DC circuit as shown in FIG. 4. By use of the circular magnetostrictive strip 32 as shown in FIG. 4 in conjunction with the AC circuit and DC circuit as shown, a torsional guided wave can be generated in a tubular member against which the circular magnetostrictive strip 32 is either dry coupled or bonded. Reflected torsional guided waves would represent defects in the tubular structure.

Figure 5:
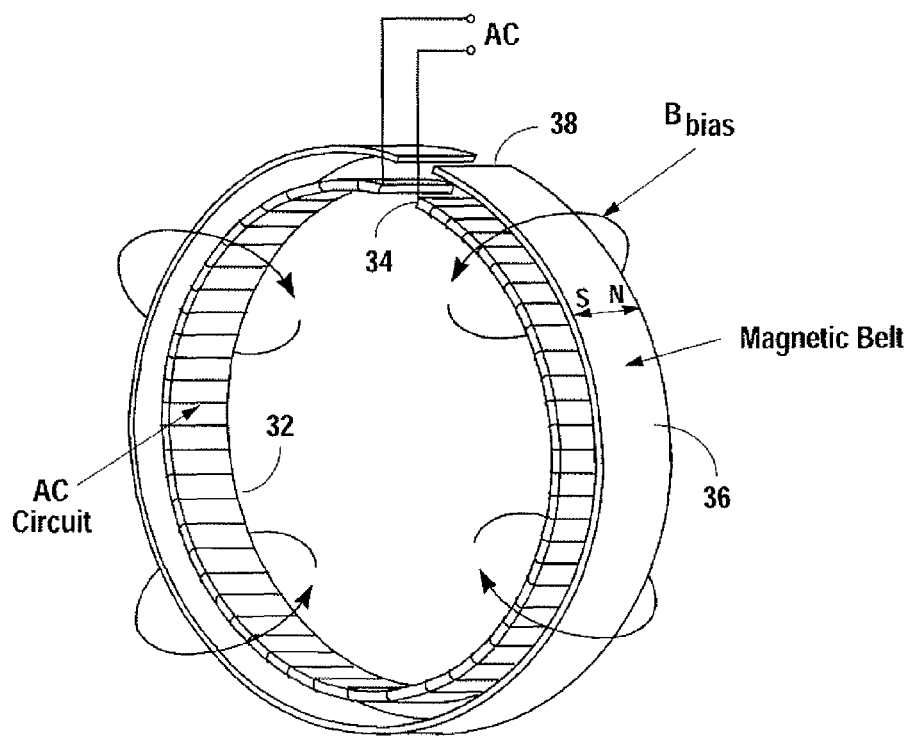
FIG. 5 is an alternative view of FIG. 4 with the DC current winding being replaced with a magnetic belt.

Referring to FIG. 5, an alternative embodiment from FIG. 4 is shown. Again, a circular magnetostrictive strip 32 is used that has a gap 34 between the ends thereof. Also, the AC circuit is wound around the short axis of the circular magnetostrictive strip 32 as illustrated in FIG. 5. However, the DC current in the DC circuit as shown in FIG. 4 have been eliminated and replaced with a magnetic belt 36 that encircles the circular magnetostrictive strip 32. The magnetic belt 36 is magnetized with the magnetic axis being along the short axis of the magnetic belt 36 as shown. Cap 38 in the magnetic belt is adjacent to the gap 34 in the circular magnetostrictive strip 32. The permanent magnetic field $B_{bias}$ encircles the circular magnetostrictive strip 32 as is shown in FIG. 5. The circular magnetostrictive strip 32 along with the magnetic belt 36 as illustrated in FIG. 5 would be used in conjunction with the control circuit shown in FIG. 2 to generate torsional guided waves in tubular structures. The permanent magnetic field $B_{bias}$ would be along the length of the tubular structure to generate torsional guided waved lengthwise along the tubular structure. This allows for the checking for defects in tubular members such as pipeline that may be buried with only periodic access points.

The circular magnetostrictive strip 32 as shown in FIGS. 4 and 5 could be made flat. In that manner, the magnetostrictive strip would be either dry coupled or bonded to the structure being tested with torsional guided waves. Concerning the magnetic belt 36 as illustrated in FIG. 5, the magnetic belt could be replaced with a series of magnets adjacent to the magnetostrictive strip 32 to generate the permanent magnetic field $B_{bias}$ therein.

By wrapping of the AC circuit around the circular magnetostrictive strip 32 as shown in FIGS. 4 and 5, it has been determined that better signal strength is generated then when the AC coil is applied adjacent to, but not wrapped around, the magnetostrictive strip. Also, the AC circuit could be divided into separate coils that can be activated individually to provide for sectional scanning of a pipe or some other large structure. The use of the circuit as shown in FIG. 4 allows for full remote control over the strength of the permanent magnetic field $B_{bias}$ as determined by the DC circuit.

Figure 6:
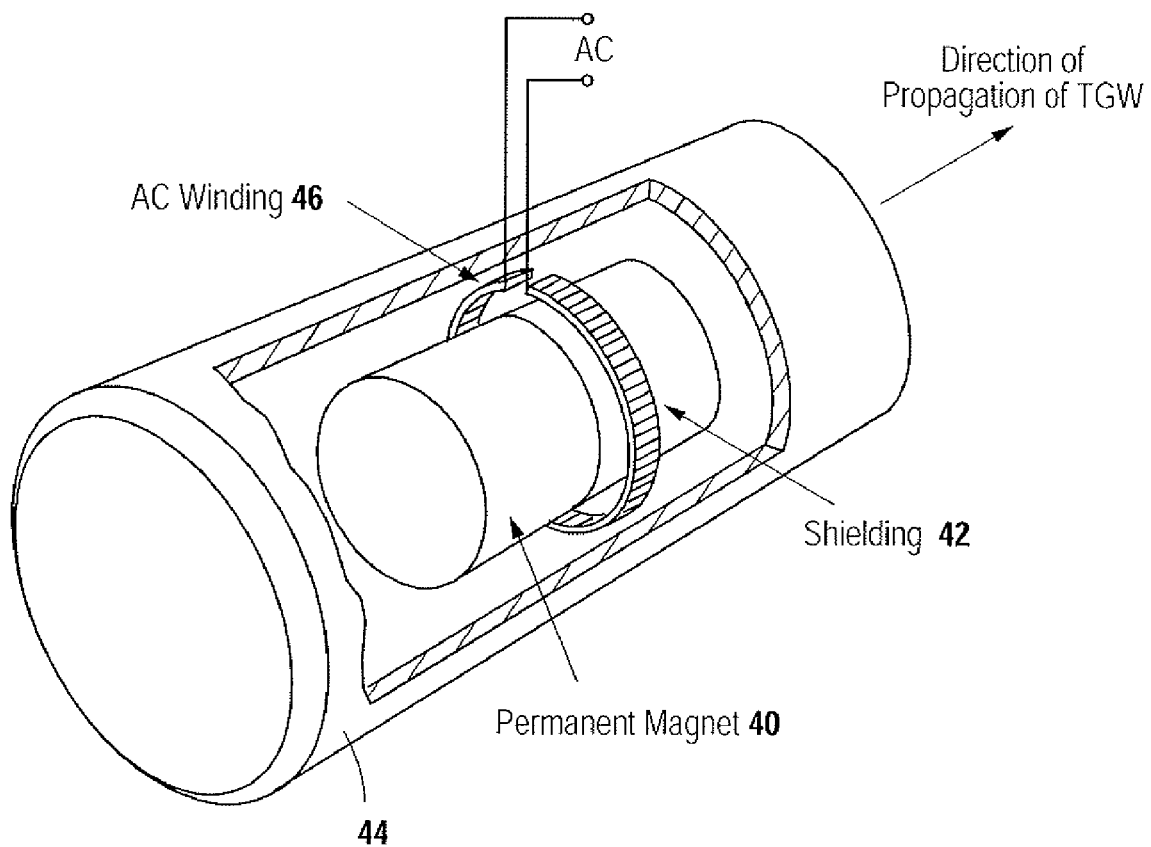
FIG. 6 is a perspective view of a shielding strip in a belt arrangement with a large permanent magnet located therein for inspection of magnetostrictive pipes using torsional guided waves.

Referring now to FIG. 6, an alternative embodiment for inspection of tubular members as shown. A permanent magnet 40 is located inside of a shielding strip 42 that has an AC winding 46 wound therearound. The use of a rather long permanent magnet 40 increases the signal to noise ratio in the tubular structure 44. In the past, it has been difficult to get a good dry coupling between a magnetostrictive strip in the inside of a tubular structure.

The larger permanent magnet 40 would magnetically saturate the wall of the tubular structure 44 in the elongated axis direction. While the tubular structure 44 needs to be of magnetostrictive materials, the walls of the tubular structure would be magnetically saturated. The AC winding 46 is wound around a shielding strip so that the portion of the winding that is on the external side of the shielding strip 42 would create the variable magnetic field $B_{AC}$ in the wall of the tubular structure 44. The AC winding 46 in combination with the permanent magnetic field $B_{bias}$ would generate torsional guided waves that propagate in the direction shown along elongated axis of the tubular structure 44. The configuration as shown in FIG. 6 would typically be used at the end of a tubular structure 44 where an electrical connection could be made to the AC winding 46.

I claim:

1. A method of nondestructive testing of a structure using magnetostrictive techniques to determine defects in the structure, said method comprising the following steps:
   first creating a permanent magnetic field at a location in said structure, said permanent magnetic field having a constant bias direction;
   applying a pulse of alternating current to an AC coil adjacent to said location;
   second creating an alternating magnetic field pulse at said location from said pulse of said alternating current, said alternating magnetic field pulse being perpendicular to said constant bias direction and parallel to a surface of said structure;
   generating a torsional guided wave from said alternating magnetic field pulse, direction of propagation of said torsional guided wave being in the same direction as said constant bias direction;
   reflecting said torsional guided wave off said defects in said structure;
   detecting said reflected torsional guided wave; and
   processing said detected reflected torsional guided wave to determine size and/or location of said defects.

2. A method of nondestructive testing of a structure using magnetostrictive techniques to determine defects in the structure as recited in claim 1 including a magnetostrictive strip dry coupled or bonded to said structure at said location.

3. A method of nondestructive testing of a structure using magnetostrictive techniques to determine defects in the structure as recited in claim 2 wherein said first creating step is caused by DC current flow adjacent said magnetostrictive strip, yet perpendicular to said direction of propogation of said torsional guided wave, but parallel to said surface of said structure.

4. A method of nondestructive testing of a structure using magnetostrictive techniques to determine defects in the structure as recited in claim 3 wherein said DC current flow is through a DC coil wound lengthwise around said magnetostrictive strip and said alternating current is through said AC coil wound perpendicular to said DC coil around said magnetostrictive strip.

5. A method of nondestructive testing of a structure using magnetostrictive techniques to determine defects in the structure as recited in claim 4 wherein said applying step including generating said pulse in a pulse generator and transmitting said pulse via a transmitter to said AC coil.

6. A method of nondestructive testing of a structure using magnetostrictive techniques to determine defects in the structure as recited in claim 5 wherein said detected reflected torsional guided wave is conditional in a signal conditioner, processed in a signal processor and analyzed in a signal analysis for said determination of said size and/or location of said defects.

7. A method of nondestructive testing of a structure using magnetostrictive techniques to determine defects in the structure as recited in claim 2 wherein said magnetostrictive strip is in a circular configuration with a gap between ends thereof and said structure is tubular.

8. A method of nondestructive testing of a structure using magnetostrictive techniques to determine defects in the structure as recited in claim 7 wherein said AC coil is wound around a short axis of said magnetostrictive strip.

9. A method of nondestructive testing of a structure using magnetostrictive techniques to determine defects in the structure as recited in claim 8 wherein said AC coil is separated into a series of coils.

10. A method of nondestructive testing of a structure using magnetostrictive techniques to determine defects in the structure as recited in claim 1 wherein said structure is tubular, said first creating step is with a large permanent magnet inside a circular shielding strip within a tubular structure, said large permanent magnet creating a magnetic bias lengthwise along said tubular structure, said second creating step being caused by said alternating current in said AC coil wound around a short axis of said shielding strip.

11. A method of nondestructive testing of a structure using magnetostrictive techniques to determine defects in the structure, said method comprising the following steps:
   securing a magnetostrictive strip to said structure;
   first creating a permanent magnetic field in said magnetostrictive strip, said permanent magnetic field having a constant bias direction perpendicular to a longitudinal axis of said magnetostrictive strip;
   applying a pulse of alternating current to an AC coil adjacent to said magnetostrictive strip;
   second creating an alternating magnetic field pulse in said magnetostrictive strip from said pulse of said alternating current, said alternating magnetic field pulse being perpendicular to said constant bias direction and parallel to a surface of said structure;
   generating a torsional guided wave in said magnetostrictive strip from said alternating magnetic field pulse, direction of propagation of said torsional guided wave being in the same direction as said constant bias direction;
   transferring said torsional guided wave from said magnetostrictive strip to said structure;
   reflecting said torsional guided waves off said defects;
   receiving said reflected torsional guided wave; and
   processing said received reflected torsional guided wave to determine size and/or location of said defects.

12. The method of nondestructive testing of a structure using magnetostrictive techniques to determine defects in the structure as recited in claim 11 wherein said securing step is by dry coupling or bonding.

13. A method of nondestructive testing of a structure using magnetostrictive techniques to determine defects in the structure as recited in claim 12 wherein said first creating step being with a series of permanent magnets for said permanent magnet field.

14. A method of nondestructive testing of a structure using magnetostrictive techniques to determine defects in the structure as recited in claim 11 wherein said AC coil is wound around a short axis of said magnetostrictive strip prior to said securing step.

15. A method of nondestructive testing of a structure using magnetostrictive techniques to determine defects in the structure as recited in claim 14 wherein said magnetostrictive strip is circular with a gap between the ends thereof and said structure is tubular.

16. A method of nondestructive testing of a structure using magnetostrictive techniques to determine defects in the structure as recited in claim 15 wherein said first creating step is by DC current flowing through a DC coil wound around a longitudinal axis of said magnetostrictive strip and perpendicular to said AC coil.

17. A method of nondestructive testing of a structure using magnetostrictive techniques to determine defects in the structure as recited in claim 11 wherein said first creating step is by a DC current flowing through a DC coil wound longitudinally around said magnetostrictive strip, but perpendicular to said AC coil, said winding occurring before said securing step.

18. A method of nondestructive testing of a structure using magnetostrictive techniques to determine defects in the structure as recited in claim 17 wherein said pulse of said alternating current is generated in a pulse generator and transmitted by a transmitter to said AC coil.

19. A method of nondestructive testing of a structure using magnetostrictive techniques to determine defects in the structure as recited in claim 18 wherein said reflected torsional guided wave is conditioned in a signal condition, processed in signal processor and analyzed in a signal analysis for said determination of said size and/or location of said defects.

\* \* \* \* \*